US009582170B2

(12) United States Patent
McCallum et al.

(10) Patent No.: US 9,582,170 B2
(45) Date of Patent: Feb. 28, 2017

(54) METHOD AND APPARATUS FOR MANAGING A CONFIGURABLE DISPLAY ENVIRONMENT

(71) Applicant: McKesson Financial Holdings, Hamilton (BM)

(72) Inventors: Leah McCallum, New Westminster (CA); Andrew Sangho Lee, New Westminster (CA); Branislav Miklos, Coquitlam (CA); Eldon Allan Wong, Vancouver (CA)

(73) Assignee: McKesson Financial Holdings, Hamilton (BM)

( * ) Notice: Subject to any disclaimer, the term of this patent is extended or adjusted under 35 U.S.C. 154(b) by 40 days.

(21) Appl. No.: 14/529,423

(22) Filed: Oct. 31, 2014

(65) Prior Publication Data

US 2016/0124619 A1 May 5, 2016

(51) Int. Cl.

| | |
|---|---|
| ***G09G 5/00*** | (2006.01) |
| ***G06F 3/0484*** | (2013.01) |
| ***A61B 6/00*** | (2006.01) |
| ***G06F 19/00*** | (2011.01) |

(52) U.S. Cl.

CPC ............ *G06F 3/04845* (2013.01); *A61B 6/00* (2013.01); *G06F 3/04842* (2013.01); *G06F 19/321* (2013.01)

(58) Field of Classification Search

None

See application file for complete search history.

(56) References Cited

U.S. PATENT DOCUMENTS

| | | | | |
|---|---|---|---|---|
| 2006/0093207 A1* | 5/2006 | Reicher | G06F 19/321 | 382/156 |
| 2008/0071895 A1* | 3/2008 | Johnson | G06F 19/321 | 709/223 |
| 2008/0183049 A1* | 7/2008 | Karkanias | G06F 19/3418 | 600/301 |
| 2013/0054467 A1* | 2/2013 | Dala | G06F 19/322 | 705/51 |
| 2015/0248749 A1* | 9/2015 | Nebosis | G06F 19/321 | 382/131 |

* cited by examiner

*Primary Examiner* — Xiao Wu
*Assistant Examiner* — Mohammad H Akhavannik
(74) *Attorney, Agent, or Firm* — Alston & Bird LLP

(57) ABSTRACT

A method, apparatus and computer program product are provided in order to manage a medical imaging study display environment. The method includes receiving, from at least one display device coupled to a medical imaging workstation, display environment context data. The method also includes extracting, by processing circuitry, metadata from a medical imaging study accessed by the medical imaging workstation, determining based at least in part on the metadata, image viewing context data, determining, based on the display environment context data and the image viewing context data, whether a display environment of the medical imaging workstation complies with one or more rules for viewing the medical imaging study, and in response to determining that the display environment of the medical imaging workstation does not comply with the one or more rules, performing at least one action before allowing viewing of the medical imaging study to proceed.

15 Claims, 5 Drawing Sheets

METHOD AND APPARATUS FOR MANAGING A CONFIGURABLE DISPLAY ENVIRONMENT

TECHNOLOGICAL FIELD

Example embodiments of the present invention relate generally to methods and devices for managing configuration of a display environment and, more particularly, to methods and apparatuses for verifying the configuration of display devices in a medical imaging system.

BACKGROUND

Advances in medical imaging technology allow for the capture of more richly detailed images than ever before. Images with an increased resolution and bit depth provide medical practitioners with the ability to discern anatomical features that might not be readily apparent at lower resolutions or color bit depth. At the same time, the ubiquity of the personal computer, a move to cost effective, off-the-shelf components for viewing of medical images, and the ability to access stored images remotely has led to an increased range of the capabilities of display environments used to view these images.

Small variations in display environments can have a dramatic impact on the ability of a medical practitioner to accurately identify particular features. Identification of these features is often essential for a correct diagnosis. A small change in the display environment such as the display resolution, color bit depth, or even ambient light in the viewing environment may result in the medical practitioner failing to note the presence or absence of a particular feature. Incorrect diagnoses may result in less efficient care, requiring additional tests and imaging studies. In the worst case, a misdiagnosis may have a material effect on patient outcomes if an otherwise treatable condition is not identified before it becomes too serious for effective treatment. Despite having a material impact on the success of the diagnosis, small changes in the display environment may not be immediately apparent to the naked eye. Through applied effort, ingenuity, and innovation, Applicant has solved many of these identified problems by developing a technical solution that is embodied by the present invention, which is described in detail below

BRIEF SUMMARY

Methods, apparatuses and computer program products are therefore provided according to example embodiments of the present invention in order to provide for managing the configuration of a display environment used to view medical images. Embodiments may include a method for managing the display environment. The method includes receiving, from at least one display device coupled to a medical imaging workstation, display environment context data, extracting, by processing circuitry, metadata from a medical imaging study accessed by the medical imaging workstation, determining based at least in part on the metadata, image viewing context data, determining, based on the display environment context data and the image viewing context data, whether a display environment of the medical imaging workstation complies with one or more rules for viewing the medical imaging study, and in response to determining that the display environment of the medical imaging workstation does not comply with the one or more rules, performing at least one action before allowing viewing of the medical imaging study to proceed. The at least one action may include presenting a pop-up notification in a graphical user interface for viewing the medical imaging study. The pop-up notification may include one or more interface controls prompting the user to accept one or more display configuration changes before viewing the medical imaging study. The at least one action may be programmatically altering at least one configuration setting of the at least one display device to cause the display environment to comply with the one or more rules. The at least one action may be sending an e-mail to an administrator notifying the administrator of the determination that the display environment does not comply with the one or more rules. The at least one display device may be a graphics card or a monitor. The display environment context data may include a resolution of a monitor and a color bit depth of the monitor. The image viewing context data may include at least one of a medical imaging device type, an image orientation, or an original resolution of an image included in the medical imaging study. The one or more rules may specify at least one of a minimum color bit depth, or a minimum display resolution. The method may include generating imaging workstation context data based on the display environment context data and the image viewing context data, and transmitting the imaging workstation context data to a remote server for processing, wherein determining whether the display environment complies with the one or more rules is performed by the remote server. At least one of the display environment context data or the image viewing context data may be stored in a markup language format.

Embodiments may also include a medical imaging workstation for managing a medical imaging study display environment. The medical imaging workstation includes display interface circuitry, image display circuitry, and context processing circuitry. The display interface circuitry is configured to obtain display environment context data from at least one display device coupled to the medical imaging workstation, and provide the display environment context data to context processing circuitry. The image display circuitry is configured to obtain image viewing context data from a medical imaging application. The image viewing context data is derived at least in part based on metadata associated with a medical imaging study accessed by the medical imaging workstation. The image display circuitry is further configured to provide the image viewing context data to the context processing circuitry. The context processing circuitry is configured to receive the display environment context data and the image viewing context data, and based at least in part on the display environment context data and the image viewing context data, perform at least one action prior to allowing viewing of the medical imaging study. The medical imaging workstation may include the at least one display device. The context processing circuitry may be further configured to transmit at least a portion of the image viewing context data and at least a portion of the display environment context data to rules engine provided by a server other than the medical imaging workstation, and to receive instructions from the rules engine to perform the at least one action, where the at least one action is determined by the rules engine based at least in part on the at least a portion of the image viewing context data and the at least a portion of the display environment context data. The at least one action may be presenting a pop-up notification in a graphical user interface for viewing the medical imaging study. The pop-up notification may include one or more interface controls prompting the user to accept one or more display configuration changes before viewing the medical imaging study. The at least one action may be programmatically altering at least one configuration setting of the at least one display device to cause the display environment to comply with the one or more rules. The at least one display device may be a graphics card or a monitor. The image viewing context data may include at least one of a medical imaging device type, an image orientation, or an original resolution of an image included in the medical imaging study.

Embodiments also include a non-transitory computer readable storage medium comprising instructions that, when executed by a processor, cause the processor to configure an apparatus. The instructions cause the processor to configure the apparatus to receive, from at least one display device coupled to a medical imaging workstation, display environment context data, to extract metadata from a medical imaging study accessed by the medical imaging workstation, to determine based at least in part on the metadata, image viewing context data, to determine, based on the display environment context data and the image viewing context data, whether a display environment of the medical imaging workstation complies with one or more rules for viewing the medical imaging study, and in response to determining that the display environment of the medical imaging workstation does not comply with the one or more rules, to perform at least one action before allowing viewing of the medical imaging study to proceed.

The above summary is provided merely for purposes of summarizing some example embodiments to provide a basic understanding of some aspects of the invention. Accordingly, it will be appreciated that the above-described embodiments are merely examples and should not be construed to narrow the scope or spirit of the invention in any way. It will be appreciated that the scope of the invention encompasses many potential embodiments in addition to those here summarized, some of which will be further described below.

BRIEF DESCRIPTION OF THE DRAWINGS

Figure 1:
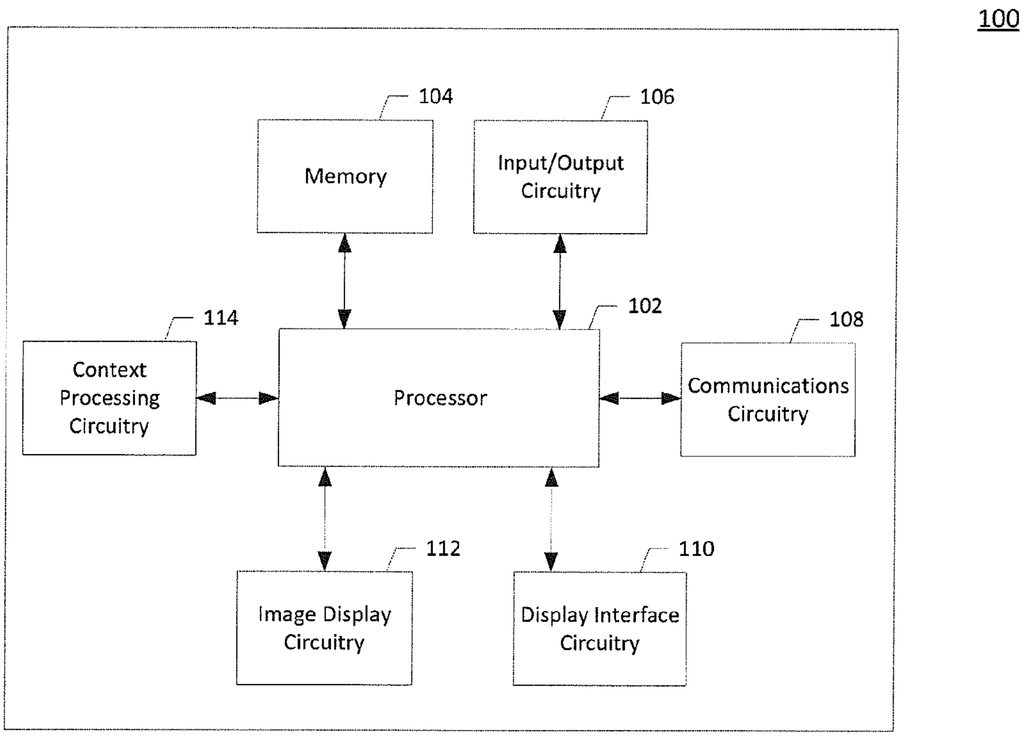
Figure 2:
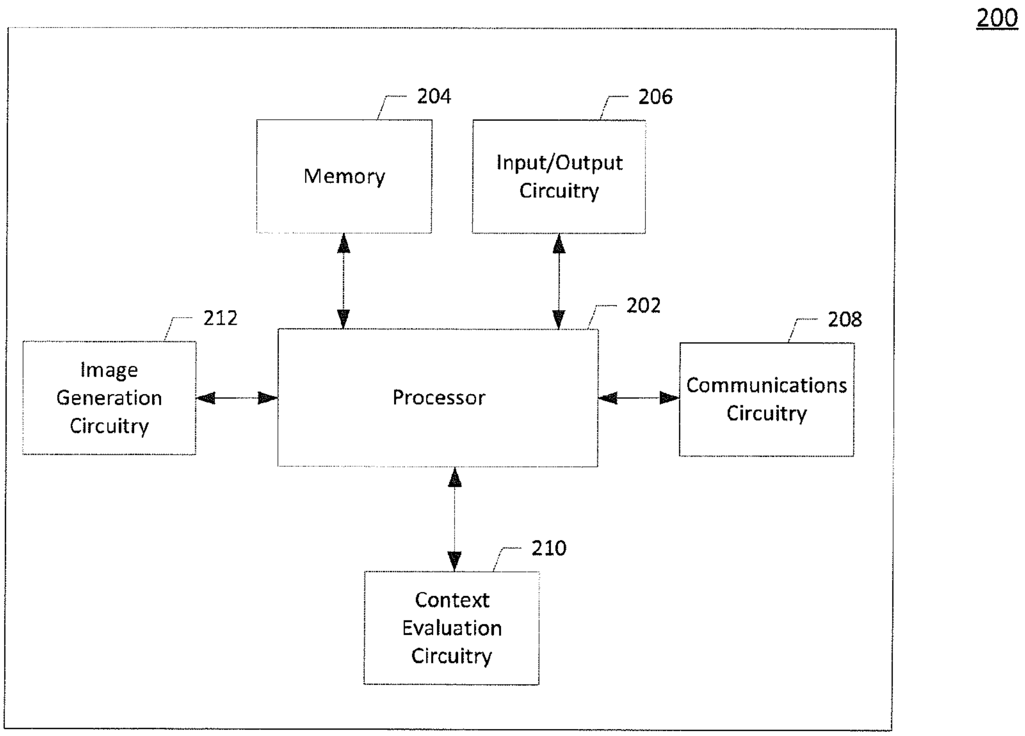
Figure 3:
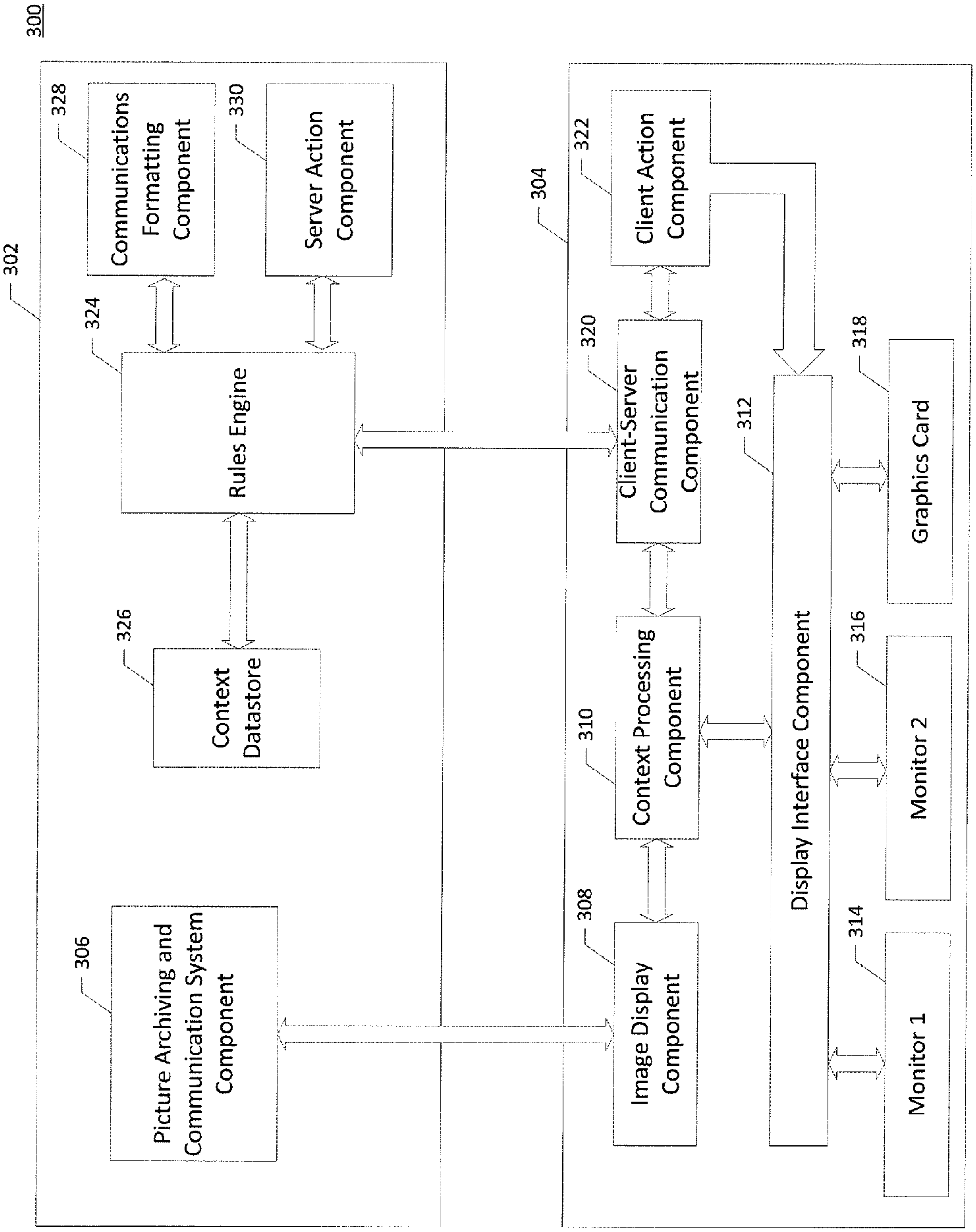
Figure 4:
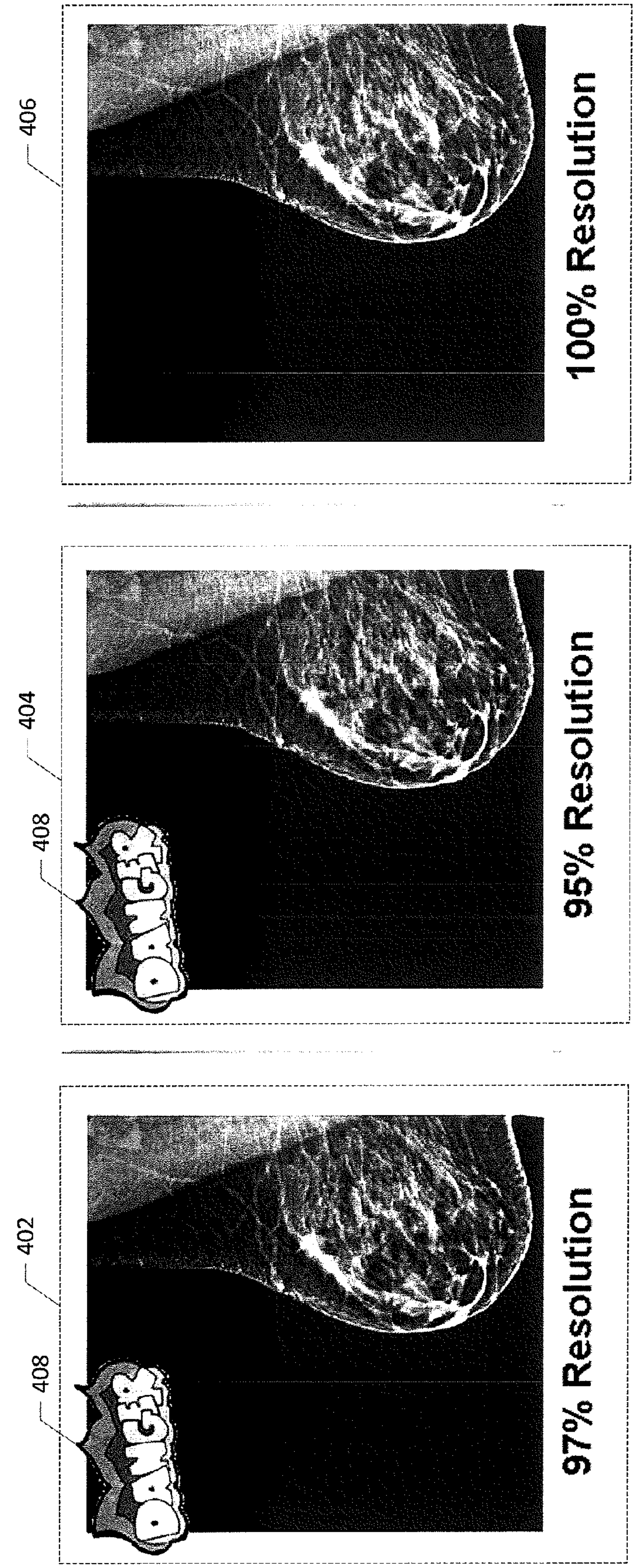
Figure 5:
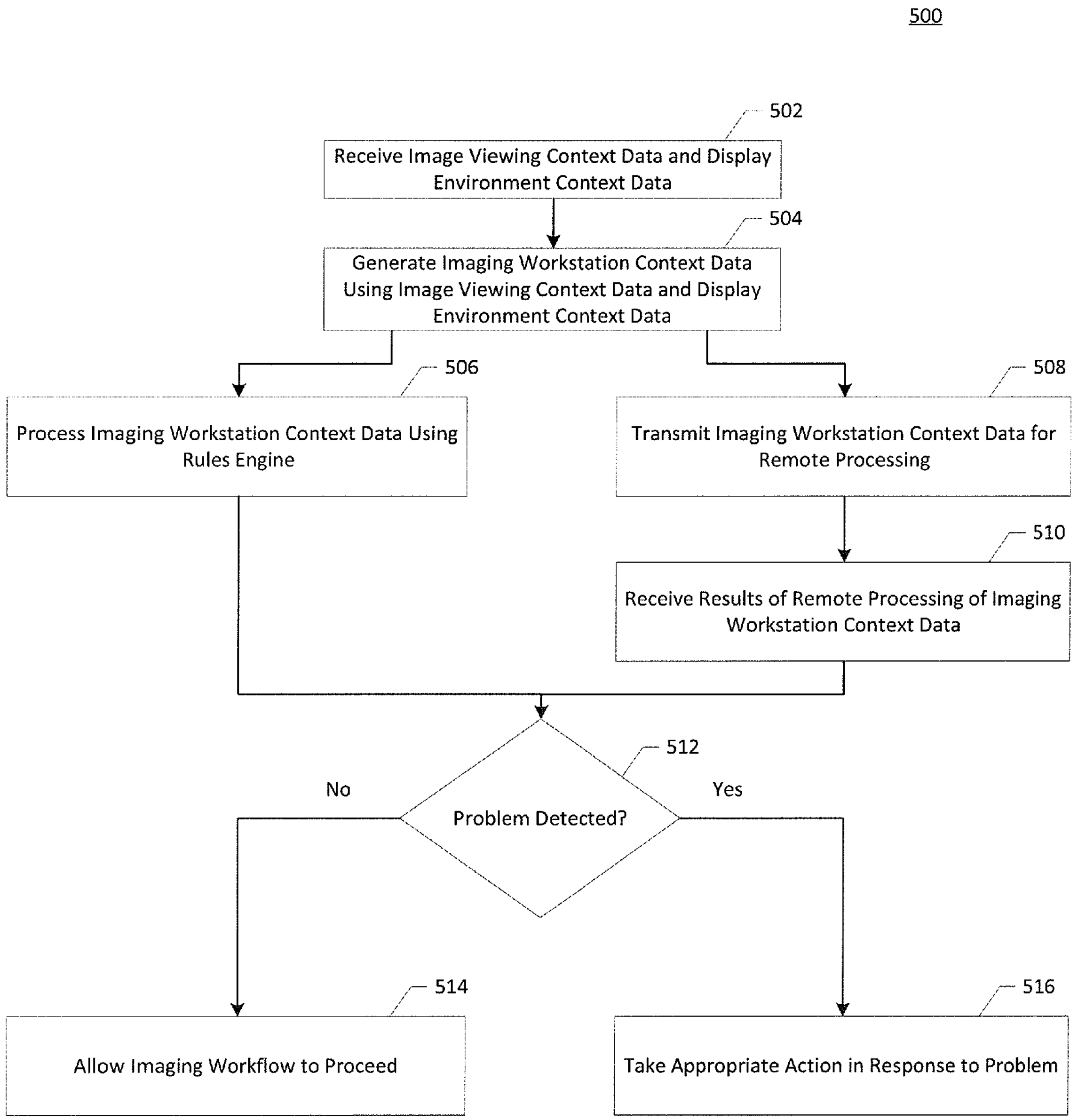
Figure 6:
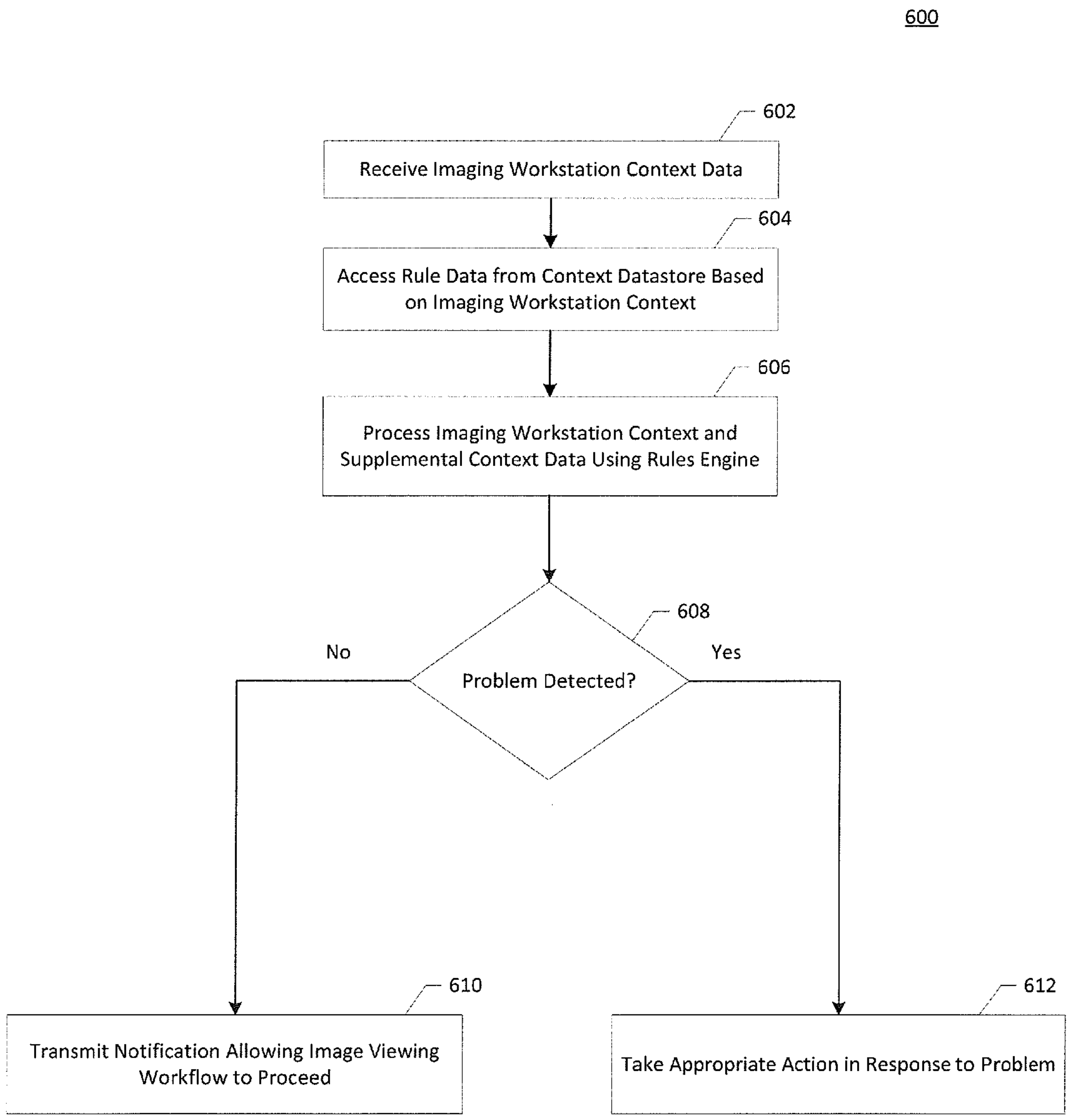

Having thus described certain embodiments of the invention in general terms, reference will now be made to the accompanying drawings, which are not necessarily drawn to scale, and wherein:

FIG. 1 is a block diagram of an apparatus for viewing medical images that may be specially configured in accordance with example embodiments of the present invention;

FIG. 2 is a block diagram of an apparatus for hosting medical images that may be specially configured in accordance with example embodiments of the present invention;

FIG. 3 is an illustration of an example data flow for managing a configuration of a display environment in accordance with example embodiments of the present invention;

FIG. 4 is an illustration of a set of medical images illustrating different display environments in accordance with example embodiments of the present invention;

FIG. 5 is a flow diagram illustrating an example of a process for managing a display environment by an imaging client device in accordance with example embodiments of the present invention; and FIG. 6 is a flow diagram illustrating an example of a process for managing a display environment of an imaging client device by a server.

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Introduction and Definitions

A method, apparatus and computer program product are provided in accordance with example embodiments of the present invention for managing a configuration of a medical imaging display environment. As noted above, the inventors have identified that small changes in the characteristics, capabilities, and configuration settings of display environments can have a significant impact on the ability of medical practitioners to provide accurate diagnoses. However, these small changes may not be readily apparent to the naked eye, such that a medical practitioner may inadvertently use a display environment that is not optimal for a given study. To address these problems, the inventors have developed methods and systems that obtain display environment context data about a display environment used for a medical imaging study to ensure that the display environment is properly configured for the medical imaging study. In some embodiments, the proper configuration settings for a medical imaging study may be dynamically determined on a study-by-study basis. For example, embodiments may automatically determine proper configuration settings upon opening a medical imaging study based on characteristics of that study (e.g., the particular patient, the resolution of the image used in the study, the orientation of the patient in the image, the type of device used to generate the image, or whether or not a contrast medium was used in the study).

If a conflict is detected between the proper configuration settings for a display environment and the actual configuration of the display environment, embodiments may take an appropriate action based on the nature of the conflict. For example, some embodiments may generate a notification to a user indicating that the display environment is improperly configured. Other embodiments may log the conflict for later review or analysis. Yet further embodiments may generate an e-mail, text message, or the like to an administrator or other user to notify the user of the conflict. Additional embodiments may prevent the study from proceeding until the conflict is addressed. Some additional embodiments may automatically adjust display settings to conform to the proper configuration setting in response to detecting the conflict.

For the purposes of this application, the term "display environment context data" refers to electronic data that indicates a status of a display hardware device (e.g., a graphics card or monitor), a display driver, a display setting, or the like. The display environment context data may be processed by a rules engine to determine if the display environment context data indicates that the display environment is properly configured for a medical imaging study. It should be appreciated that, in some embodiments, display environment context data can also include sensor data indicating external factors that may contribute to the ability of the practitioner to view a medical imaging study, such as the amount of ambient light in the display room, a color of a display bezel, the time of day, or the like.

For the purposes of this application, the term "image viewing context data" refers to electronic data that indicates one or more characteristics of a particular selected image or images, or a particular selected imaging study or imaging studies. The image viewing context data may be processed by a rules engine to determine a set of proper configuration settings for a display environment to properly view the selected image or study.

For the purposes of this application, the term "medical imaging study" refers to an image or set of images captured by a medical imaging device such as an x-ray, computed tomography (CT) scan, magnetic resonance imaging scanner, or the like. The term should be understood to refer to both single, isolated images and sets of images. In some embodiments, the medical imaging study will include a set of metadata describing the file format of the image, the original capture resolution of the image, the type of device used to capture the image, the date the image was captured, a patient associated with the captured image, a viewing orientation of the image, a particular anatomical part of the patient represented in the image, one or more diagnostic codes, one or more procedure codes, or the like. In some embodiments, the medical imaging study may be stored in a Digital Imaging and Communications in Medicine (DICOM) file format. In some embodiments, the medical imaging study may be stored in other image formats such as JPEG, BMP, GIF, PNG, or the like.

Example Client Apparatus

FIG. 1 illustrates a block diagram of an apparatus 100 in accordance with some example embodiments. The apparatus 100 may be any computing device capable of managing a configuration of a display environment for a medical imaging study as described herein. For example, the apparatus 100 may be implemented as any device capable of viewing or displaying a medical imaging study, such as a server (e.g., an application server implemented as a standalone or rack-mounted server), a desktop computer, a laptop computer, a personal digital assistant, a tablet computer, a netbook computer, a picture archiving and communication system (PACS) workstation, or the like. The apparatus 100 may be operable to determine display environment context data for a display environment associated with the apparatus 100 (e.g., a configuration of a monitor or other display device, a graphics card, and the like coupled to the apparatus 100), and to verify that the display environment context data complies with a proper configuration for a medical imaging study. The apparatus 100 may further determine the proper configuration for the medical imaging study based on image viewing context data derived from the medical imaging study and/or metadata for the medical imaging study. The apparatus 100 may further communicate the image viewing context data and the display environment context data to a server other than the apparatus 100 and receive notifications or other events related to the image viewing context data and the display environment context data. Accordingly, it will be appreciated that the apparatus 100 may comprise an apparatus configured to implement and/or otherwise support implementation of various example embodiments described herein.

It should be noted that the components, devices or elements illustrated in and described with respect to FIG. 1 below may not be mandatory and thus some may be omitted in certain embodiments. Additionally, some embodiments may include further or different components, devices or elements beyond those illustrated in and described with respect to FIG. 1.

As illustrated in FIG. 1, an apparatus 100 may include a processor 102, a memory 104, input/output circuitry 106, communications circuitry 108, display interface circuitry 110, image viewing circuitry 112 context processing circuitry 114. The apparatus 100 may be configured to execute the operations described below with respect to FIGS. 3 and 5. Although these components 102-114 are described with respect to functional limitations, it should be understood that the particular implementations necessarily include the use of particular hardware. It should also be understood that certain of these components 102-114 may include similar or common hardware. For example, two sets of circuitry may both leverage use of the same processor, network interface, storage medium, or the like to perform their associated functions, such that duplicate hardware is not required for each set of circuitry. The use of the term "circuitry" as used herein with respect to components of the apparatus should therefore be understood to include particular hardware configured to perform the functions associated with the particular circuitry as described herein.

The term "circuitry" should be understood broadly to include hardware and, in some embodiments, software for configuring the hardware. For example, in some embodiments, "circuitry" may include processing circuitry, storage media, network interfaces, input/output devices, and the like. In some embodiments, other elements of the apparatus 100 may provide or supplement the functionality of particular circuitry. For example, the processor 102 may provide processing functionality, the memory 104 may provide storage functionality, the communications circuitry 108 may provide network interface functionality, and the like.

In some embodiments, the processor 102 (and/or co-processor or any other processing circuitry assisting or otherwise associated with the processor) may be in communication with the memory 104 via a bus for passing information among components of the apparatus. The memory 104 may be non-transitory and may include, for example, one or more volatile and/or non-volatile memories. In other words, for example, the memory may be an electronic storage device (e.g., a computer readable storage medium). The memory 104 may be configured to store information, data, content, applications, instructions, or the like, for enabling the apparatus to carry out various functions in accordance with example embodiments of the present invention.

The processor 102 may be embodied in a number of different ways and may, for example, include one or more processing devices configured to perform independently. Additionally or alternatively, the processor may include one or more processors configured in tandem via a bus to enable independent execution of instructions, pipelining, and/or multithreading. The use of the term "processing circuitry" may be understood to include a single core processor, a multi-core processor, multiple processors internal to the apparatus, and/or remote or "cloud" processors.

In an example embodiment, the processor 102 may be configured to execute instructions stored in the memory 104 or otherwise accessible to the processor. Alternatively or additionally, the processor may be configured to execute hard-coded functionality. As such, whether configured by hardware or software methods, or by a combination thereof, the processor may represent an entity (e.g., physically embodied in circuitry) capable of performing operations according to an embodiment of the present invention while configured accordingly. Alternatively, as another example, when the processor is embodied as an executor of software instructions, the instructions may specifically configure the processor to perform the algorithms and/or operations described herein when the instructions are executed.

In some embodiments, the apparatus 100 may include input/output circuitry 106 that may, in turn, be in communication with processor 102 to provide output to the user and, in some embodiments, to receive an indication of a user input. The input/output circuitry 106 may comprise a user interface and may include a display and may comprise a web user interface, a mobile application, a client device, a kiosk, or the like. In some embodiments, the input/output circuitry 106 may also include a keyboard, a mouse, a joystick, a touch screen, touch areas, soft keys, a microphone, a speaker, or other input/output mechanisms. The processor and/or user interface circuitry comprising the processor may be configured to control one or more functions of one or more user interface elements through computer program instructions (e.g., software and/or firmware) stored on a memory accessible to the processor (e.g., memory 104, and/or the like).

The communications circuitry 108 may be any means such as a device or circuitry embodied in either hardware or a combination of hardware and software that is configured to receive and/or transmit data from/to a network and/or any other device, circuitry, or module in communication with the apparatus 100. In this regard, the communications circuitry 108 may include, for example, a network interface for enabling communications with a wired or wireless communication network. For example, the communications circuitry 108 may include one or more network interface cards, antennae, buses, switches, routers, modems, and supporting hardware and/or software, or any other device suitable for enabling communications via a network. Additionally or alternatively, the communication interface may include the circuitry for interacting with the antenna(s) to cause transmission of signals via the antenna(s) or to handle receipt of signals received via the antenna(s).

The display interface circuitry 110 includes hardware configured to interface with one or more sources of display environment context data such as a display device, a graphics card, or a display driver. The display interface circuitry 110 may function to send and receive data to and from various display components of the apparatus, such as described above with respect to the input/output circuitry 106. The display interface circuitry 110 may thus function as a device driver or drivers for the sources of display environment context data. The display interface circuitry 110 includes a processor configured to implement one or more application programming interfaces (APIs) and/or graphics libraries (e.g., Open Graphics Library®) for communicating with the sources of display environment context data. The display interface circuitry 110 may obtain, via hardware configured to communicate with the display components of the apparatus, display environment context data.

The display environment context data that may be obtained by the display interface circuitry 110 may vary depending upon the type of the source of display environment context data. For example, a monitor may provide display environment context data relating to a display size, a display pixel width, a maximum resolution, a current resolution, a maximum color bit depth, a current color bit depth, a maximum display lifetime, a current display lifetime, a maximum refresh rate, a model identifier, a hardware revision number, a serial number, a manufacturer name, a firmware revision identifier, and the like. A graphics card may provide display environment context data relating to a processor clock frequency, a memory clock frequency, a number of shader pipelines, a number of pixel pipelines, a firmware revision identifier, a manufacturer identifier, a model identifier, or the like. A display driver may provide display environment context data relating to a release date of the display driver, a version number of the display driver, or the like. The display interface circuitry 110 may obtain the display environment context data by causing execution of one or more application programming interface (API) functions as implemented by the various sources of display environment context data to obtain the display environment context data. The display interface circuitry 110 may utilize processing circuitry, such as the processor 102, to perform these actions. It should also be appreciated that, in some embodiments, the display interface circuitry 110 may include a separate processor, specially configured field programmable gate array (FPGA), or application specific interface circuit (ASIC) to interface with display devices. The display interface circuitry 110 is therefore implemented using hardware components of the apparatus configured by either hardware or software for implementing these planned functions.

The image display circuitry 112 includes hardware configured to access and display a medical imaging study. The image display circuitry 112 may include a processor configured to execute an application that accesses a medical imaging study from a memory and displays the medical imaging study via a display. The image display circuitry 112 may also include hardware configured to obtain image viewing context data related to the medical imaging study. For example, the image display circuitry 112 may identify various characteristics of the medical imaging study as image viewing context data such as a type of the study, the patient anatomical feature that is the subject of the study, a particular patient associated with the medical imaging study, a resolution of an image stored in the medical imaging study, an orientation of the medical imaging study, a modality of the medical imaging study, a user viewing the medical imaging study, a practitioner schedule associated with the client, or the like. In some embodiments the information described above may be obtained from metadata associated with the medical imaging study, while in other embodiments some or all of said data may be determined programmatically, such as through the use of optical character recognition techniques, image processing techniques, inference from patient medical records, or the like. The image display circuitry 112 may utilize processing circuitry, such as the processor 102, to perform these actions. It should also be appreciated that, in some embodiments, the image display circuitry 112 may include a separate processor, specially configured field programmable gate array (FPGA), or application specific interface circuit (ASIC) to provide for viewing a medical imaging study. In some embodiments where the medical imaging study is stored in a remote storage location, the image display circuitry 112 may comprise a network interface or interface with the communications circuitry 108 to obtain the medical imaging study from the remote storage location. The image display circuitry 112 is therefore implemented using hardware components of the apparatus configured by either hardware or software for implementing these planned functions.

The apparatus 100 further comprises context processing circuitry 114. The context processing circuitry 114 includes hardware configured to format and package a set of context data for use in managing a display environment during a medical imaging operation. The set of context data may include display environment context data obtained from display interface circuitry 110 as described above and image viewing context data obtained from image viewing circuitry 112 as described above. The context processing circuitry 114 may be further configured to analyze the set of context data to identify a proper configuration for a medical imaging study, compare the proper configuration to a display environment configuration identified by the display environment context data, and take an appropriate action based on the conflict. The context processing circuitry 114 may utilize processing circuitry, such as the processor 102, to perform these actions. The context processing circuitry 114 may be configured to transmit the set of context data to a server for remote analysis. In some embodiments, the context processing circuitry 114 may transmit the set of context data via the communications circuitry 108. It should also be appreciated that, in some embodiments, the context processing circuitry 114 may include a separate processor, specially configured field programmable gate array (FPGA), or application specific interface circuit (ASIC) to generate the context data. The context processing circuitry 114 is therefore implemented using hardware components of the apparatus configured by either hardware or software for implementing these planned functions.

As will be appreciated, any such computer program instructions and/or other type of code may be loaded onto a computer, processor or other programmable apparatus's circuitry to produce a machine, such that the computer, processor other programmable circuitry that execute the code on the machine create the means for implementing various functions, including those described herein.

It is also noted that all or some of the information presented by the example displays discussed herein can be based on data that is received, generated and/or maintained by one or more components of apparatus 100. In some embodiments, one or more external systems (such as a remote cloud computing and/or data storage system) may also be leveraged to provide at least some of the functionality discussed herein.

FIG. 2 illustrates a block diagram of an apparatus 200 for managing configuration of a display environment for a medical imaging operation in accordance with some example embodiments. The apparatus 200 may function as a server device, such as a Picture Archiving and Communication System (PACS) configured to host medical imaging studies, provide the medical imaging studies to a client, receive a set of context data from the client, and take appropriate action in response to detecting a conflict between a client display environment and a set of proper configuration settings for a medical imaging study being viewed on the client. As illustrated in FIG. 2, the apparatus 200 may include a processor 202, a memory 204, an input/output circuitry 206, a communications circuitry 208, context evaluation circuitry 210, and image generation circuitry 212. The apparatus 200 may be configured to execute the operations described below with respect to FIGS. 3 and 6. The functioning of the processor 202, the memory 204, the input/output circuitry 206, and the communication circuitry 208 may be similar to the similarly named components described above with respect to FIG. 1. For the sake of brevity, additional description of these components is omitted.

The context evaluation circuitry 210 includes hardware configured to receive context information from a client and evaluate the context information to identify conflicts between a display environment of the client device and a proper configuration for a medical imaging study being performed on the client device. The context information may be received via a network interface, such as provided by the communications circuitry 208. It should also be appreciated that, in some embodiments, the context evaluation circuitry 210 may include a separate processor, specially configured field programmable gate array (FPGA), or application specific interface circuit (ASIC) to evaluate the context data. The context evaluation circuitry 210 is therefore implemented using hardware components of the apparatus configured by either hardware or software for implementing these planned functions.

The image generation circuitry 212 includes hardware configured to store, access, and provide medical image studies. The image generation circuitry 212 may include an archival function of a PACS, whereby medical image studies are stored and provided to client devices in response to a request from the client device for the particular medical imaging study. The image generation circuitry 212 may be configured to receive and respond to such requests. In some embodiments, the image generation circuitry 212 includes hardware for receiving medical imaging studies directly from a medical imaging device without intervening storage and/or archiving. In some embodiments, the image generation circuitry 212 includes hardware for receiving an image from a medical imaging device and processing the image to generate a medical imaging study. The image generation circuitry 212 may receive requests for and provide medical images via the communications circuitry 208. It should also be appreciated that, in some embodiments, the image generation circuitry 212 may include a separate processor, specially configured field programmable gate array (FPGA), or application specific interface circuit (ASIC) to receive and provide medical imaging studies. The image generation circuitry 212 is therefore implemented using hardware components of the apparatus configured by either hardware or software for implementing these planned functions.

As described above and as will be appreciated based on this disclosure, embodiments of the present invention may be configured as methods, mobile devices, backend network devices, and the like. Accordingly, embodiments may comprise various means including entirely of hardware or any combination of software and hardware. Furthermore, embodiments may take the form of a computer program product on at least one non-transitory computer-readable storage medium having computer-readable program instructions (e.g., computer software) embodied in the storage medium. Any suitable computer-readable storage medium may be utilized including non-transitory hard disks, CD-ROMs, flash memory, optical storage devices, or magnetic storage devices.

Having now described an apparatus configured to implement and/or support implementation of various example embodiments, features of several example embodiments will now be described. It will be appreciated that the following features are non-limiting examples of features provided by some example embodiments. Further, it will be appreciated that embodiments are contemplated within the scope of disclosure that implement various subsets or combinations of the features further described herein. Accordingly, it will be appreciated that some example embodiments may omit one or more of the following features and/or implement variations of one or more of the following features.

Example Display Environment Configuration Management Data Flow

FIG. 3 is an illustration of an example data flow 300 for providing management of a display environment configuration in a medical imaging operation in accordance with example embodiments of the present invention. The data flow 300 illustrates communications between and among components of a server 302 and a client 304 to ensure that the client 304 is properly configured to perform a medical imaging study viewing operation. The server 302 and the client 304 may be implemented as independent computing devices in communication with one another. For example, the server 302 may be implemented by an apparatus, such as the apparatus 200 described above with respect to FIG. 2, and the client 304 may be implemented by an apparatus, such as the apparatus 100 described above with respect to FIG. 1.

The server 302 may act as a PACS, hosting one or more medical imaging studies and providing said medical imaging studies in response to requests from client devices. To this end, the server 302 may include a PACS component 306. The PACS component 306 may serve to store, maintain, and provide access to medical imaging studies according to a variety of imaging modalities, formats, and the like. The PACS component 306 may provide said medical imaging studies to the client 304. The medical imaging studies may be provided to the client by the PACS component 306 in a variety of manners. For example, the medical imaging studies may be transmitted directly to the client 304 as a download. Alternatively, the medical imaging studies may be hosted by the PACS component 306 and provided as a web page. In some embodiments, the PACS component 306 is implemented by image generation circuitry 212 as described above with respect to FIG. 2.

An image display component 308 of the client 304 may receive the medical imaging study provided by the PACS component 306. The image display component 308 may be configured to provide medical imaging study viewing services via the client 304. For example, the image display component 308 may implement a viewing application that provides for display of the medical imaging study via a graphical user interface, or the image display component 308 may provide a browser for viewing web-based medical imaging studies. The image display component 308 may be further configured to derive image viewing context data from the medical imaging study. The image viewing context data may be provided to a context processing component 310. The image display component 308 may be implemented by image display circuitry 112 as described above with respect to FIG. 1.

A display interface component 312 may communicate with one or more display devices 314-318 to derive display environment context data and to provide the display environment context data to the context processing component 310. Some embodiments may include a single display interface component 312 for communication with a plurality of display devices, while other embodiments may have a single display interface component 312 for each display device. The display interface component 312 may include a library, web service, application programming interface, manufacturer tool, or the like for obtaining the display environment context data. In some embodiments, the display environment context data provided by each display device 314-318 may depend upon features implemented by a manufacturer of the display device. For example, the display interface component 312 may be a tool or application programming interface provided as a function of a device driver of the display device. Particular examples of display interface components 312 may include "Barco Medical Self Exam" offered by Barco N.V.®, and "RadiCS" offered by Ezio®. In some embodiments, tools offered by device manufacturers may provide insufficient display environment context data to appropriately configure a display environment to view a medical imaging study. In such cases, the display interface component 312 may include additional functions or applications to extend basic functionality offered by the device manufacturer to convert information provided by the device manufacturer into a format suitable for use as display environment context data. In some embodiments, the display interface component 312 formats data received from each of the display devices into a common format. For example, the display interface component 312 may convert data received directly from the devices 314-318 into a markup language format, with tags of the markup language indicating particular data types and values. In some embodiments, the display interface component 312 may obtain data for use as display environment context data from other sources, such as log files, registry settings, environment variables, or the like.

Different display devices may provide different types of display environment context data. For example, a liquid crystal display (LCD) monitor may provide different types of display environment context data from a cathode ray tube (CRT) monitor, and a graphics card may provide different types of display environment context data from a monitor device. As a particular example, a given monitor may provide information describing version information for drivers installed for the monitor, the operational lifetime of the monitor, the amount of time the monitor has been powered on, the refresh rate of the monitor, the maximum color bit depth of the monitor, the maximum resolution of the monitor, the current color bit depth of the monitor, the current resolution of the monitor, and the like. A given graphics card may provide information relating to a display driver version for the graphics card, the processor clock frequency of the graphics card, the memory clock frequency of the graphics card, the firmware version of the graphics card, the fan speed of the graphics card, or the like. The display interface component may provide the display environment context data to the context processing component 310.

In some embodiments, the display interface component 312 is also operable to adjust configuration settings associated with the display devices 314-318. For example, the display interface component 312 may receive instructions to change configuration settings to comply with a proper configuration for a particular medical imaging study.

The context processing component 310 may receive the image viewing context data and display environment context data and generate a set of imaging workstation context data representing both sets of data. The imaging workstation context data may be presented in a markup language format. For example, the imaging workstation context data may be presented as follows:

TABLE 1

```
<CONTEXT Date="Feb. 7th, 2014 10:00AM" User="Doctor ABC" TriggerType="Open
Study">
  <IMAGE_VIEWER>
    <PATIENT>
      <MRN>1234</MRN>
    </PATIENT>
    <STUDY>
```

TABLE 1-continued

```
      <ACCESSION>6789</ACCESSION>
    </STUDY>
  </IMAGE_VIEWER>
  <DISPLAY_ENVIRONMENT>
    <DISPLAY_ITEM Type="Monitor">
      <MANUFACTURER>BARCO</MANUFACTURER>
      <MODEL>MDRC-1119 HB</MODEL>
      <MEGA_PIXELS>8</MEGA_PIXELS>
      <COLOUR_SUPPORT>30 bit</COLOUR_SUPPORT>
      <UNIFORM_LUMINENCE>YES</UNIFORM_LUMINENCE>
      <DATE_OF_MANUFACTURE>Week 15 of 2013</DATE_OF_MANUFACTURE>
   </DISPLAY_ITEM>
    <DISPLAY_ITEM Type="Monitor">
      <MANUFACTURER>BARCO</MANUFACTURER>
      <MODEL>MDCC-6130</MODEL>
      <MEGA_PIXELS>4</MEGA_PIXELS>
      <SIGNAL_INPUT_TYPE>Digital</SIGNAL_INPUT_TYPE>
      <DATE_OF_MANUFACTURE>Week 17 of 2013</DATE_OF_MANUFACTURE>
    </DISPLAY_ITEM>
  </DISPLAY_ENVIRONMENT>
</CONTEXT>
```

In some embodiments, the context processing component 310 may obtain the display environment context data and the image viewing context data in response to a user opening a medical imaging study using the image display component 308. When the medical imaging study is opened, the context processing component 310 may retrieve the relevant display environment context data from the display interface component 312 to reflect the display environment at the time the medical imaging study is first displayed. The context processing component 310 may be implemented by context processing circuitry 114 as described above with respect to FIG. 1.

The context processing component 310 may provide context information to a client-server communication component 320. The context information may be provided to the client-server communication component 320 as separate sets of context information (e.g., a set of display environment context data and a set of image viewing context data) or a single set of imaging workstation context data. The client-server communication component 320 may provide the context information to a rules engine 324 on the server 302. In some embodiments, the context processing component 310 may also perform an analysis of the context information to determine if the image viewing context data and the display environment context data indicate that the client device is properly configured to perform a medical imaging operation. It should be appreciated that some embodiments may employ the context processing component 310 solely as a conduit for transmission of information to the rules engine 324 and for reception and processing of instructions from the rules engine 324, while in other embodiments evaluation of the context may be performed wholly or partially by the context processing component 310. If the client device is not properly configured, the context processing component 310 may send a notification to the client-server communication component 320. Based on the notification, the client-server communication component 320 may communicate with a client action component 322 to take an appropriate action. The client-server communication component 320 may be implemented by context processing circuitry 114 acting in concert with communication circuitry 108 as described above with respect to FIG. 1.

The rules engine 324 may process the context information received from the client-server communication module 320 to evaluate whether the client 304 is properly configured to perform the medical imaging operation. In some embodiments, the rules engine 324 may be responsible for the rule configuration and processing of the context data that is transmitted from the client 304. In some embodiments, the rules engine may be implemented as an instance of Qualitative Intelligence & Communication System (QICS™), by McKesson®.

In some embodiments, the rules engine 324 may access a context datastore 326 to obtain additional data for evaluating the received context. For example, the rules engine 324 may determine a particular set of rules for evaluating whether display environment context data is appropriate for a particular medical imaging study. In some embodiments, the context datastore 326 may include a set of constraints on display environment context data for a given set of image viewing context data. If the display environment context data does not meet the constraints for the particular image viewing context data, then the rules engine 324 may perform certain actions. The particular actions performed by the rules engine 324 in response to detecting a conflict between the display environment data and constraints for the image viewing context data may be determined based on the particular constraint that is violated. For example, if a display has exceeded its operational lifetime, embodiments may notify an administrator or technician to replace the display via a communications formatting component 328 configured to send an e-mail or other notification. The rules may include triggers, expressions (e.g., Boolean operators), and actions. For example, the rules may include a trigger indicating when the rule processing (i.e. evaluate condition expression) occurs. Expressions may join together particular triggers to determine when the rule action occurs. The actions may specify the particular actions to be taken in response to the rule being triggered. Similarly to the context data, in some embodiments the rules may be implemented via a markup language. An example rule configuration may be implemented as follows:

TABLE 2

```
<RULE Name="Sub-Optimal Display Environment Alert">
  <TRIGGER Type="Open Study" />
  <CRITERIA Expression="[TOKEN1] AND [TOKEN2] AND ([TOKEN3] OR [TOKEN4])
">
    <CRITERION Token="1">ExamCode = 'Mammo'</CRITERION>
    <CRITERION Token="2">Type = 'DBT'</CRITERION>
    <CRITERION Token="3">Monitor_Manufacturer != 'Barco'</CRITERION>
    <CRITERION Token="4">Monitor_MegaPixels < 8</CRITERION>
  </CRITERIA>
  <ACTIONS>
    <ACTION Type="Popup">
      <RECIPIENT>User In Trigger Context</RECIPIENT>
      <TEXT>Warning: Display Environment Not Optimal!</TEXT>
    </ACTION>
  </ACTIONS>
</RULE>
```

In some embodiments, the rules engine 324 may be configured to cause a particular action to occur via a server action component 330. The server action component 330 may perform various actions at the direction of the rules engine. For example, the server action component 330 may cause a PACS component 306 of the server 302 to halt a medical imaging operation if a conflict is detected between the display environment context data and constraints for a medical imaging operation. In some embodiments, the rules engine 324 may inform the client-server communication component 320 of the conflict.

In some embodiments, the context datastore 326 includes other external sources of context data. For example, in some embodiments the context datastore may include a medical practitioner scheduling, personnel, or human resources system that provides context data indicating which practitioners are on a particular rotation on a particular day or at a particular time. In such cases, embodiments may allow particular practitioners to specify certain rules or constraints for their imaging operations. In some embodiments, a particular specialty or experience level of the practitioner may also be taken into account when deciding what display environment context data indicates an acceptable display environment for a particular study. Certain medical practitioners may calibrate image viewing modalities in a certain manner, based on assumptions that the display environment meets certain minimum standards (e.g., regulatory or site standards) and/or best-practices hardware and/or settings.

While the rules engine 324 is depicted as a component of the server 302, it should be appreciated that in some embodiments the rules engine 324 could be located on or as a component of the client 304 in addition to or as an alternative to the server-based implementation depicted in FIG. 3. The rules engine 324 may be implemented by context evaluation circuitry 210 acting in concert with communications circuitry 208 as described above with respect to FIG. 2.

The client action component 322 may receive instructions from the client-server communication component 320. The instructions may be originally generated by the rules engine 324, and/or the context processing component 310. The client action component 322 may cause various changes or actions on the client 304 in response to receiving notification of a conflict. These changes may include, for example, displaying a pop-up notification warning a user of the conflict, causing a medical imaging operation to halt until the conflict is corrected, or altering settings to ensure the display environment conforms to the requirements for the medical imaging study, such as by sending a notification or instructions to the display interface component 312 to modify settings for one or more of the display devices 314-318. Other example changes may include prompting a confirmation dialogue to the user prompting whether the user wishes to change their display settings to the appropriate values. The user may be presented with an option to cancel the image operation with no further action taken, and an option to accept the configuration changes which may then be performed automatically. The client action component 322 may be implemented by context processing circuitry 114 as described above with respect to FIG. 1.

Example Imaging Operation

FIG. 4 depicts an example illustration 400 highlighting an example of the output of an exemplary embodiment of the present invention. The illustration 400 depicts three images 402, 404, and 406 at different display resolutions. The first image 402 and the second image 404 depict images shown at 97% and 95% of their original resolution, respectively. For example, the first image 402 and the second image 404 may be displayed on monitors with a lower maximum resolution. While the differences in these images may not be perceptible to the naked eye, the reduction in resolution could result in a medical practitioner missing an important feature of the image. It should also be appreciated that while the images have a different resolution, the images in the instant example have been stretched to display as the same size, further complicating the ability of a practitioner to identify when the display environment is appropriate. Such a scenario might be common where any displayed image is stretched to fill the available screen space on a given monitor, resulting in deficiencies that are too minute to detect to the naked eye. As such, each of the first image 402 and the second image 404 are depicted with a warning notification 408, highlighting the fact that the images are not displayed at full resolution. The third image 406 is displayed at full resolution, and thus no warning is displayed.

Example Processes for Managing Configuration of a Display Environment

FIG. 5 is a flow diagram illustrating an example of a process 500 for managing a display environment by an imaging client device in accordance with example embodiments of the present invention. The process 500 is operable to gather context data relating to a medical imaging study, including display environment context data and image viewing context data, to use the gathered context data to ensure the display environment is properly configured, and to take appropriate action in the event the display environment is not properly configured. Embodiments of the process may be performed by an apparatus, such as the apparatus 100 described with respect to FIG. 1, and as part of a display environment configuration management operation as depicted with respect to FIG. 3.

At action 502, image viewing context data and display environment context data is received. As described above with respect to FIGS. 1-4, the image viewing context data may be received as part of an image viewing operation, and the display environment context data may be received from a display interface component. The context data may be received by means for receiving context data, such as the context processing circuitry 114 as described above with respect to FIG. 1.

At action 504, a set of imaging workstation context data is generated based on the image viewing context data and the display environment context data. The set of imaging workstation context data may be generated by means for generating imaging workstation context data, such as the context processing circuitry 114 as described above with respect to FIG. 1. The set of imaging workstation context data may be processed locally, proceeding to action 506, and/or remotely, proceeding to action 508. At action 506, a rules engine is used to process the set of imaging workstation context data. Processing the set of imaging workstation context data may include evaluating the display environment context data and the image viewing context data according to a set of rules. Processing the set of imaging workstation context data may be performed by means for processing the set of imaging workstation data, such as the context processing circuitry 114 described above with respect to FIG. 1, or the context evaluation circuitry 210 described above with respect to FIG. 2.

At action 508, the imaging workstation context data is transmitted to a remote recipient, such as the server 302 describes above with respect to FIG. 3 or the apparatus 200 described above with respect to FIG. 2. The imaging workstation context data may be transmitted by means for doing so, such as communications circuitry 108 as described above with respect to FIG. 1.

At action 510, results of remote processing of the imaging workstation context data may be received. Results of the remote processing may be received by communications circuitry 108 as described above with respect to FIG. 1.

At action 512, the process 500 splits based on whether a problem (i.e., a conflict between the display environment context data and the requirements for the medical imaging operation) is detected. If a problem is not detected, the process 500 proceeds to action 514. If a problem is detected, the process 500 proceeds to action 516.

At action 514, the process 500 may allow the medical imaging operation to proceed without further action, since no conflict was detected. In some embodiments, allowing the medical imaging operation to proceed may include marking a graphical user interface as "correct" or "authorized", or otherwise providing an indication to a user that the display environment is suitable for performing the medical imaging operation.

At action 516, if a problem is detected, the process 500 may take appropriate action. As described above with respect to FIGS. 1-4, appropriate action may include preventing the medical imaging operation from proceeding, providing a warning notification to the user, sending a notification to a user or external node, or automatically adjusting display settings to bring the display into compliance with the requirements of the medical imaging study. Appropriate action may be taken by means for taking appropriate action, such as the context processing circuitry 114 acting in concert with the display interface circuitry 110 as described above with respect to FIG. 1.

FIG. 6 is a flow diagram illustrating an example of a process 600 for managing a display environment of an imaging client device by a server. The process 600 is operable to allow a server, such as a PACS system, to take appropriate action in response to detection of a problem with a client display environment. In some embodiments, the server may implement a rules engine for evaluating imaging workstation context data provided by a client. Embodiments of the process 600 may be performed by an apparatus, such as the apparatus 200 described above with respect to FIG. 2.

At action 602, a set of imaging workstation context data is received from a client. The set of imaging workstation context data may be received by means for doing so, such as the communications circuitry 208 described above with respect to FIG. 2.

At action 604, rule data is accessed from a context datastore to process the imaging workstation context data. For example, particular rules may be accessed from the context datastore based on a type of medical imaging study indicated in the imaging workstation context data. At action 606, the rule data is used to process the imaging workstation context data to determine if the display environment of the client is in compliance with the particular medical imaging study being performed. The rule data may be accessed and the imaging workstation context data may be processed by means for doing so, such as the context evaluation circuitry 210 described above with respect to FIG. 2.

At action 608, a determination is made as to whether the processing performed at action 606 indicates a problem in the client display environment. If a problem is not detected, the process 600 may transmit a notification to the client at action 610 indicating that the medical imaging study may proceed. The notification may be transmitted by means for doing so, such as the communications circuitry 208 described above with respect to FIG. 2. If a problem is detected, the process 600 proceeds to action 612 and appropriate action is taken. As described above, appropriate action may include sending a notification to an administrator, sending a notification to the client device, or the like as described above. The appropriate action may be taken by means for doing so, such as the context evaluation circuitry 210 acting in concert with the communications circuitry 208 as described above with respect to FIG. 2.

It will be understood that each element of the flowcharts, and combinations of elements in the flowcharts, may be implemented by various means, such as hardware, firmware, processor, circuitry, and/or other devices associated with execution of software including one or more computer program instructions. For example, one or more of the procedures described above may be embodied by computer program instructions. In this regard, the computer program instructions which embody the procedures described above may be stored by a memory 104 of an apparatus employing an embodiment of the present invention and executed by a processor 102 of the apparatus. As will be appreciated, any such computer program instructions may be loaded onto a computer or other programmable apparatus (e.g., hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture the execution of which implements the function specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowchart blocks.

Accordingly, blocks of the flowchart support combinations of means for performing the specified functions and combinations of operations. It will also be understood that one or more blocks of the flowchart, and combinations of blocks in the flowchart, can be implemented by special purpose hardware-based computer systems which perform the specified functions, or combinations of special purpose hardware and computer instructions.

In some embodiments, certain ones of the operations above may be modified or further amplified. Furthermore, in some embodiments, additional optional operations may be included. Modifications, additions, or amplifications to the operations above may be performed in any order and in any combination.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method for managing a medical imaging study display environment comprising:

receiving, from at least one display device coupled to a medical imaging workstation, display environment context data, wherein the display environment context data comprises display resolution;

extracting, by processing circuitry, metadata from a medical imaging study accessed by the medical imaging workstation, wherein the metadata describes one or more of the original capture resolution of the image, the file format of the image, the type of device used to capture the image, the date the image was captured, a patient associated with the captured image, a viewing orientation of the image, a particular anatomical part of the patient represented in the image, one or more diagnostic codes, or one or more procedure codes;

determining based at least in part on the metadata from the medical image study, image viewing context data, wherein the viewing context data comprises medical image resolution of at least one image stored in the medical image study;

determining, based on the display environment context data and the image viewing context data, whether a display environment of the medical imaging workstation complies with one or more rules for viewing the medical imaging study, wherein the rules relate at least in part to a compatibility between the display resolution of the display device and the medical image resolution of the at least one image; and in response to determining that the display environment of the medical imaging workstation does not comply with the one or more rules related to a compatibility between the display resolution of the display device and the medical image resolution of the at least one image, providing for presentation of a pop-up notification comprising one or more interface controls prompting the user to accept one or more display configuration changes needed to comply with the one or more rules, and causing the display configuration changes to be implemented on the display device before providing for presentation of the medical imaging study.

2. The method of claim 1, further comprising sending an e-mail to an administrator notifying the administrator of the determination that the display environment does not comply with the one or more rules.

3. The method of claim 1, wherein the at least one display device is a graphics card or a monitor.

4. The method of claim 1, wherein the display environment context data further comprises a color bit depth of the monitor.

5. The method of claim 1, wherein the image viewing context data further comprises at least one of a medical imaging device type, an image orientation, or an original resolution of an image included in the medical imaging study.

6. The method of claim 1, wherein the one or more rules specify at least one of a minimum color bit depth, or a minimum display resolution.

7. The method of claim 1, further comprising:

generating imaging workstation context data based on the display environment context data and the image viewing context data; and transmitting the imaging workstation context data to a remote server for processing, wherein determining whether the display environment complies with the one or more rules is performed by the remote server.

8. The method of claim 1, wherein at least one of the display environment context data or the image viewing context data is stored in a markup language format.

9. A medical imaging workstation for managing a medical imaging study display environment comprising:

display interface circuitry configured to:

obtain display environment context data from at least one display device coupled to the medical imaging workstation, wherein the display environment context data comprises display resolution; and provide the display environment context data to context processing circuitry;

image display circuitry configured to:

obtain image viewing context data comprising medical image resolution of at least one image stored in the medical image study from a medical imaging application, the image viewing context data derived at least in part based on metadata associated with a medical imaging study accessed by the medical imaging workstation, wherein the metadata describes one or more of the original capture resolution of the image, the file format of the image, the type of device used to capture the image, the date the image was captured, a patient associated with the captured image, a viewing orientation of the image, a particular anatomical part of the patient represented in the image, one or more diagnostic codes, or one or more procedure codes; and provide the image viewing context data to the context processing circuitry; the context processing circuitry, configured to:

receive the display environment context data and the image viewing context data;

determine rules relating at least in part to a compatibility between the display resolution of the display device and the medical image resolution of the at least one image; and in response to determining that the display environment of the medical imaging workstation does not comply with the one or more rules related to a compatibility between the display resolution of the display device and the medical image resolution of the at least one image, provide for presentation of a pop-up notification comprising one or more interface controls prompting the user to accept one or more display configuration changes needed to comply with the one or more rules, and cause the display configuration changes to be implemented on the display device before providing for presentation of the medical imaging study.

10. The medical imaging workstation of claim 9, further comprising the at least one display device.

11. The medical imaging workstation of claim 9, wherein the context processing circuitry is further configured to:

transmit at least a portion of the image viewing context data and at least a portion of the display environment context data to rules engine provided by a server other than the medical imaging workstation; and receive instructions from the rules engine to cause the display configuration changes to be implemented based at least in part on the at least a portion of the image viewing context data and the at least a portion of the display environment context data.

12. The medical imaging workstation of claim 9, further comprising programmatically altering at least one configuration setting of the at least one display device to cause the display environment to comply with the one or more rules.

13. The medical imaging workstation of claim 9, wherein the at least one display device is a graphics card or a monitor.

14. The medical imaging workstation of claim 9, wherein the image viewing context data comprises at least one of a medical imaging device type, an image orientation, or an original resolution of an image included in the medical imaging study.

15. A non-transitory computer readable storage medium comprising instructions that, when executed by a processor, cause the processor to configure an apparatus to:

receive, from at least one display device coupled to a medical imaging workstation, display environment context data, wherein the display environment context data comprises display resolution;

extract metadata from a medical imaging study accessed by the medical imaging workstation, wherein the metadata describes one or more of the original capture resolution of the image, the file format of the image, the type of device used to capture the image, the date the image was captured, a patient associated with the captured image, a viewing orientation of the image, a particular anatomical part of the patient represented in the image, one or more diagnostic codes, or one or more procedure codes;

determine based at least in part on the metadata from the medical image study, image viewing context data, wherein the viewing context data comprises medical image resolution of at least one image stored in the medical image study;

determine, based on the display environment context data and the image viewing context data, whether a display environment of the medical imaging workstation complies with one or more rules for viewing the medical imaging study, wherein the rules relate at least in part to a compatibility between the display resolution of the display device and the medical image resolution of the at least one image; and in response to determining that the display environment of the medical imaging workstation does not comply with the one or more rules related to a compatibility between the display resolution of the display device and the medical image resolution of the at least one image, providing for presentation of a pop-up notification comprising one or more interface controls prompting the user to accept one or more display configuration changes needed to comply with the one or more rules, and causing the display configuration changes to be implemented on the display device before providing for presentation of the medical imaging study.

* * * * *